(12) United States Patent
Sullivan et al.

(10) Patent No.: US 11,776,212 B1
(45) Date of Patent: Oct. 3, 2023

(54) ANATOMICALLY CONFORMING APPARATUSES, SYSTEMS, AND METHODS, AND APPLICATIONS THEREOF

(71) Applicant: Oceanit Laboratories, Inc., Honolulu, HI (US)

(72) Inventors: Christopher Sullivan, Honolulu, HI (US); Matthew Williams, Honolulu, HI (US); Matthew Sullivan, Honolulu, HI (US)

(73) Assignee: Oceanit Laboratories, Inc., Honolulu, HI (US)

( * ) Notice: Subject to any disclaimer, the term of this patent is extended or adjusted under 35 U.S.C. 154(b) by 0 days.

(21) Appl. No.: 17/214,548

(22) Filed: Mar. 26, 2021

Related U.S. Application Data (60) Provisional application No. 63/000,434, filed on Mar. 26, 2020, provisional application No. 63/000,437, filed on Mar. 26, 2020.

(51) Int. Cl.
| | | |
|---|---|---|
| *G06T 17/20* | (2006.01) | |
| *G06T 19/20* | (2011.01) | |
| *G06F 18/23* | (2023.01) | |
| *B33Y 80/00* | (2015.01) | |

(52) U.S. Cl.
CPC .............. *G06T 17/20* (2013.01); *B33Y 80/00* (2014.12); *G06F 18/23* (2023.01); *G06T 19/20* (2013.01); *G06T 2207/30201* (2013.01)

(58) Field of Classification Search
None
See application file for complete search history.

(56) References Cited

U.S. PATENT DOCUMENTS

| | | | | |
|---|---|---|---|---|
| 10,471,703 | B2* | 11/2019 | Bachelder | A61M 16/0605 |
| 10,740,921 | B2* | 8/2020 | Znamenskiy | G06T 7/60 |
| 2016/0361511 | A9* | 12/2016 | Karpas | A61M 16/0683 |
| 2019/0043255 | A1* | 2/2019 | Somasundaram | G06T 17/20 |
| 2021/0209865 | A1* | 7/2021 | Cunliffe | G06F 18/2431 |

OTHER PUBLICATIONS

Schreinemakers et al., "Oxygen Mask Related Nasal Integument and Osteocartilagenous Disorders in F-16 Fighter Pilots," PLoS One, vol. 8, No. 3 (2013).

(Continued)

*Primary Examiner* — Nurun Flora
(74) *Attorney, Agent, or Firm* — Fresh IP PLC; Clifford D. Hyra; Aubrey Y Chen (57) ABSTRACT

The present invention is generally directed to anatomically conforming apparatuses, and the creation, design, and fitting of such apparatuses. In at least one embodiment, the present invention relates to masks that require a conformal fit to a user's face, including, but not limited to, respirator and breathing masks, oxygen masks for both civil and military pilots, ventilation masks used in hazardous environments, and the like. One or more methods for clustering facial scans to design a finite set of mass-producible masks is also described, such that each individual in a given population can be assigned at least one mask in the set of masks that is anatomically conforming to that individual's specific facial geometry. Also described are one or more methods for fitting a face mask to a specific individual based on a 3-D scan of that individual's face.

22 Claims, 7 Drawing Sheets

(56) References Cited

OTHER PUBLICATIONS

Lee et al., Ergonomic Design and Evaluation of a Pilot Oxygen Mask, Proc. Human Factors and Ergonomics Soc. 57th Annual Meeting 2013.
Patel et al, "3D morphable face models revisited," 2009 IEEE Conference on Computer Vision and Pattern Recognition (2009).
Clark et al, "The CN2 induction algorithm," Machine Learning 3.4: 261-83 (1989).

* cited by examiner

ANATOMICALLY CONFORMING APPARATUSES, SYSTEMS, AND METHODS, AND APPLICATIONS THEREOF

CROSS-REFERENCE TO RELATED APPLICATIONS

This application claims the benefit of U.S. Provisional Application No. 63/000,434, filed Mar. 26, 2020, and U.S. Provisional Application No. 63/000,437, filed Mar. 26, 2020, each of which is hereby incorporated by reference in its respective entirety.

STATEMENT REGARDING FEDERALLY SPONSORED RESEARCH OR DEVELOPMENT

The invention described herein was made with U.S. government ("Government") support under Contract No. N68335-19-C-0010, awarded by the U.S. Department of the Navy. As a result, the Government has certain rights in this invention.

FIELD OF THE INVENTION

The application relates generally to anatomically conforming apparatuses, and the creation, design, and fitting of such apparatuses. In particular, the present application relates to masks that require a conformal fit to a user's face, including, but not limited to, respirator and breathing masks, oxygen masks for both civil and military pilots, ventilation masks used in hazardous environments, and the like.

BACKGROUND

Apparatuses that conform to one or more portions of a wearer's physical anatomy (a property referred to herein as "anatomically conforming" or "anatomically conformal") are necessary in many different applications across a variety of fields. Purely as a non-limiting example, respirator and breathing masks of all types depend on an anatomically conformal fit to the user's face for both adequate function and adequate comfort.

Currently, these masks and other worn apparatuses are produced in a set of standard sizes to enable mass production, and under the assumption that any individual in the general population will fit at least one of the standard sizes. However, ill-fitting masks are a common problem, including, as a non-limiting example, for users of non-invasive ventilation systems such as, for instance, continuous (and bi-level) positive airway pressure systems, as well as civilian and military pilot oxygen mask systems, causing discomfort and injury when the masks are cinched down to achieve functional seals. As an additional non-limiting example, ill-fitting respirator masks worn in hazardous environments expose the users to environmental hazards, including, for instance, particles, microorganisms, fumes, and vapors.

Given the foregoing, there exists a significant need for new anatomically conforming apparatuses that are also cost-effective, including, but not limited to, face masks for various industrial, medical, civil, and military applications, as well as new technologies capable of creating, designing, and fitting such anatomically conforming apparatuses.

SUMMARY

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description.

In general, the present invention is directed to anatomically conforming apparatuses, systems, and methods, including, as a non-limiting example, masks that require a conformal fit to a user's face, such as, for instance, continuous positive airway pressure (CPAP) masks and oxygen masks for civil and military pilots. At least one embodiment of the present invention relates more specifically to the optimized design, development, and fitting of fitted apparel and medical appliances for a specific population.

In at least one embodiment of the current invention, a set of three-dimensional ("3-D") facial scans from a population are processed with an adaptive clustering algorithm, or other multi-objective optimization method, to identify and/or design a smaller subset of facial profiles for which complimentary contoured face masks, including, for example, oral-nasal masks, are designed to ensure a comfortable and anatomically conforming fit. This allows a limited number of face masks to be designed and/or produced to better fit each individual in an entire population, while still being mass-produced. Prospective users can scan their faces with 3-D scanning systems, have their facial profiles processed and matched against a landscape of faces in a population database, and have these profiles matched to the most closely-fitting mask through an adaptive clustering analysis that updates clustering multi-objective optimization objective functions. Furthermore, users are matched to an anatomically conforming mask that best fits their specific body geometry using the same clustering analysis that also estimates metrics of fit quality such as peak contact pressure, pressure distribution, or overall comfort. The process described in this paragraph for producing a subset of anatomically conformal products and fitting them to users can be performed for other anatomical areas besides faces, including, but not limited to, feet, hands, and other body parts and areas.

One of skill in the art will appreciate that the aforementioned clustering is an approach whereby a set of objects are grouped in a way such that objects that are more similar to each other are in the same group, and that an object in any given group is more similar to another such object in the same group than to one or more other objects in one or more other groups. The challenge in clustering analysis is to determine, in some cases, the best method or methods to group objects to achieve one or more particular objectives. As a result, clustering can be an iterative process whereby the clustering process itself is modified to optimize the one or more particular objectives. It should be appreciated that one or more iterative steps may be partially or fully automated using artificial intelligence (AI) methods, including, for example, reinforcement learning with deep neural networks, which are capable of continuously learning and improving based on additional data.

It should further be appreciated that one or more embodiments of the present invention reduces or eliminates the need for tightening a wearable apparatus, such as, for instance, a face mask, until there is a seal, in order to prevent any leaks. Purely as a non-limiting example, the production and delivery of face masks that provide oxygen to military pilots may involve a set of five mass-produced masks from which users hope to get their best fit. In order to achieve functional performance, the user must tighten the mask until there is a seal. This leads to physical ailments, including, for example, nasal integument and osteocartilagenous disorders. (See Schreinemakers et al., "Oxygen Mask Related Nasal Integument and Osteocartilagenous Disorders in F-16 Fighter Pilots," PLoS One, Vol. 8, No. 3 (2013), available at https://www.ncbi.nlm.nih.gov/pmc/articles/PMC3591424/, which is herein incorporated by reference in its entirety). The same issues, involving physical injuries due to tightening a mask, are also present in the use of non-invasive ventilation systems, such as continuous (and bi-level) positive airway pressure systems, respirator systems, and the like.

Further, the present invention describes at least one method for achieving cost-effective mass production of face masks, including, for instance, oral-nasal type masks, that are designed to better fit a population using statistically driven anthropometric design. While additive manufacturing is currently being used to produce a number of commercial products, there is currently no substitute for mass production using high pressure silicone injection molding for many medical appliances and commercial products that take advantage of properties of silicone rubbers including, for example, biocompatibility and minimal off gassing. One of skill in the art will appreciate the various advantages of silicone. The silicon-oxygen chemical structure of silicone produces an elastomer that has special properties which include biocompatibility, excellent temperature and chemical resistance, as well as good mechanical and electrical properties. Furthermore, it can be produced in a near-transparent form.

The present invention additionally describes at least one method of designing and/or producing a face mask using algorithms described herein that achieve better fit and performance across a population of users using statistically driven anthropometric design. Three-dimensional scanning has become ubiquitous and is available on mobile phone platforms, providing a convenient way to capture anthropometric data for multiple purposes. The accuracy of this data is sub-millimeter and more than sufficient for use in creating form-fitting appliances and apparatuses that match the contours of the user, enabling more comfortable apparatuses than currently exist in the marketplace.

These and further and other objects and features of the invention are apparent in the disclosure, which includes the above and ongoing written specification, as well as the drawings.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art.

DETAILED DESCRIPTION

The present invention is more fully described below with reference to the accompanying figures. The following description is exemplary in that several embodiments are described (e.g., by use of the terms "preferably," "for example," or "in one embodiment"); however, such should not be viewed as limiting or as setting forth the only embodiments of the present invention, as the invention encompasses other embodiments not specifically recited in this description, including alternatives, modifications, and equivalents within the spirit and scope of the invention. Further, the use of the terms "invention," "present invention," "embodiment," and similar terms throughout the description are used broadly and not intended to mean that the invention requires, or is limited to, any particular aspect being described or that such description is the only manner in which the invention may be made or used. Additionally, the invention may be described in the context of specific applications; however, the invention may be used in a variety of applications not specifically described.

In the several figures, like reference numerals may be used for like elements having like functions even in different drawings. The embodiments described, and their detailed construction and elements, are merely provided to assist in a comprehensive understanding of the invention. Thus, it is apparent that the present invention can be carried out in a variety of ways, and does not require any of the specific features described herein. Also, well-known functions or constructions are not described in detail since they would obscure the invention with unnecessary detail. Any signal arrows in the drawings/figures should be considered only as exemplary, and not limiting, unless otherwise specifically noted. Further, the description is not to be taken in a limiting sense, but is made merely for the purpose of illustrating the general principles of the invention, since the scope of the invention is best defined by the appended claims.

It will be understood that, although the terms first, second, etc. may be used herein to describe various elements, these elements should not be limited by these terms. These terms are only used to distinguish one element from another. Purely as a non-limiting example, a first element could be termed a second element, and, similarly, a second element could be termed a first element, without departing from the scope of example embodiments. As used herein, the term "and/or" includes any and all combinations of one or more of the associated listed items. As used herein, the singular forms "a", "an," and "the" are intended to include the plural forms as well, unless the context clearly indicates otherwise. It should also be noted that, in some alternative implementations, the functions and/or acts noted may occur out of the order as represented in at least one of the several figures. Purely as a non-limiting example, two figures shown in succession may in fact be executed substantially concurrently or may sometimes be executed in the reverse order, depending upon the functionality and/or acts described or depicted.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

In general, the word "instructions," as used herein, refers to logic embodied in hardware or firmware, or to a collection of software units, possibly having entry and exit points, written in a programming language, such as, but not limited to, SWIFT, Objective C, Java, Lua, C, C++, or C#. A software unit may be compiled and linked into an executable program, installed in a dynamic link library, or may be written in an interpreted programming language such as, but not limited to, BASIC, Perl, or Python. It will be appreciated that software units may be callable from other units or from themselves, and/or may be invoked in response to detected events or interrupts. Software units configured for execution on computing devices by their hardware processor(s) may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. Generally, the instructions described herein refer to logical modules that may be combined with other modules or divided into sub-modules despite their physical organization or storage.

In this disclosure, references are made to users and to their client computing devices/platforms. In general, the users and their computing devices are conceptually interchangeable. Therefore, it is to be understood that where an action is shown or described as being performed by a user, in various implementations and/or circumstances the action may be performed entirely by the user's computing device or by the user, using their computing device to a greater or lesser extent (e.g., a user may type out a response or input an action, or may choose form preselected responses or actions generated by the computing device). Similarly, where an action is shown or described as being carried out by a computing device, the action may be performed autonomously by that computing device or with more or less user input, in various circumstances and implementations.

Generally, the present invention is directed towards anatomically conforming apparatuses, systems, and methods, including, as a non-limiting example, face masks and oral-nasal masks. This present invention further relates to the optimized design, development, and fitting of wearable apparatuses, apparel, and medical appliances for a population.

The present invention, in at least one embodiment, provides a method that uses 3-D anatomical scan data to automatically design a limited set of physically conformal and interfacing, or wearable, apparatuses, including, for instance, face masks and oral-nasal masks, of specific sizes and shapes that fit a population of users with more comfort and a better air-tight seal than currently available. It should be appreciated that such wearable apparatuses, designed and/or produced in the aforementioned fashion, can be mass produced.

Additionally, at least one embodiment of the invention is capable of automatically determining the best-matching and most optimally-fitting oral-nasal mask for a user from a set of existing oral-nasal masks. Further, at least one embodiment of the invention is able to predict the contact pressure distribution of a specific oral-nasal mask design as worn by a particular user.

This invention in its various embodiments also comprises a method for intelligently creating a set of anatomically conformal apparatuses that will fit a population of users by utilizing 3-D anatomical scans and an iterative clustering algorithm with a proper physically measurable objective function. This objective function can be evaluated using a computer model of the physical world to accelerate the process of evolving clustering parameters so as to create the best way to group anatomical features, such that apparatuses designed to be anatomically conformal to a given user are well-fitting, comfortable, and seal well if the need for airtight and/or watertight sealing exists.

The creation of designs for anatomically conforming, mass-producible wearable apparatuses, including, for example, face masks and oral-nasal masks, can be done automatically from a database of facial scans, such that a small set of the designs fits a large population of users. It should be appreciated that such anatomically conforming apparatuses could include other wearable items besides face masks, including, for example, footwear, gloves and/or other handwear, earplugs, and jeans, pants, bodysuits, and/or other clothing. Scans may therefore be done with respect to any anatomical area that is of interest. Purely as a non-limiting example, designing anatomically conforming shoes can be done automatically from one or more sets of representative foot scans. With reference to the purely non-limiting example of the creation of designs for anatomically conforming oral-nasal masks, the prospective users' facial scans are grouped using a clustering method that starts out with an initial basis for clustering. This initial basis for clustering could be, for instance, measurements such as mouth width and the distance from the nose bridge to the spot below the lower lip. The success of using this basis for clustering is then evaluated using either an actual, physical measurement of mask fit, such as the required force necessary to produce an airtight seal for a modest pressure level or a computer-based model of fit evaluation as the objective function, such as, for example, total overlap volume or underlap volume between the mask surface and the face surface. The space of clustering bases is searched by modifying or substituting bases (i.e., modifying or switching landmarks for measuring distances) and re-evaluating the objective function. Such a search process could be done using any number of search methods, including, for instance, Monte Carlo tree searches or genetic algorithms. Once an optimum basis for clustering is found, oral-nasal masks are designed for each cluster in the population, using the centermost facial scan in the cluster as the basis for the oral-nasal mask design.

One optimal basis for clustering is the fewest number of designed objects, or apparatuses, that fit the total population with an acceptable level of fit. In other words, an optimal basis is the combination of landmarks that are used to successfully cluster the population into the lowest number of designs. Purely as a non-limiting example, if 2 psi is a measurement threshold for comfort or good fit, an optimal basis occurs if no point on a user's face experiences a force amount greater than 2 psi. Alternatively, an optimal basis occurs if at least 95% of the users have a force amount equal to, or less, than 2 psi.

It should be appreciated that this procedure results in a set of designs that covers the entire population of users that need to be fitted. Users that need a mask have their faces scanned to produce a 3-D map of their face, which is then processed with the clustering algorithm to determine which cluster the scan belongs to, and, as a result, which oral-nasal mask is the best fit.

One of skill in the art will appreciate that clustering is a statistical method that utilizes measurable features of some object or system to cluster together similar objects or systems. In the case of faces, clustering can produce a set of masks that can be mass-produced but that would be more anatomically conforming than current, generically-fitted masks. Purely as a non-limiting example, if a clustering method shows that sufficiently fitting masks could service a large population from a set of, for instance, 20 different shapes, then these masks could be mass-produced, and each user in the population could determine their own best fit through a 3-D face scan and compatibility algorithm, as described above and elsewhere in the instant specification.

By clustering the facial features of different individuals, a set number of masks can be produced that encompass faces with a large range of anatomical geometry with a certain level of accuracy. Given enough groupings of masks, it is possible to create a finite set of masks that fits the entire population with an acceptable level of comfort or other fit metric. Such metrics may include, for instance, a minimum level of fit or a maximum level of applied pressure to achieve a fit.

Purely as a non-limiting example, utilization of the Bosphorus database set of 299 people with neutral facial expressions, different clusters based on 22 landmarks identified on each individual's face have been identified. With this database, it was found that around 20-30 masks will encompass most of the facial geometries in the database with a relatively low mismatch between the mask and the most outlying face of the cluster. Mismatch means both (1) the physical difference in shape between the mask and a given face, measured using the linear distance between the mask surface and the face surface, and (2) the physical difference between facial landmarks, measured using the linear distance between any two or more landmarks.

It should be appreciated that other databases besides the Bosphorus database can also be used to find the least number of masks required to fit every person in the database. That is, the present invention can be utilized with any database of anatomical scans, or even across more than one desired database. It should be appreciated that the database(s) used depends on the specific population for which anatomically conforming apparatuses are to be designed. A sufficient number of scans, such as, for instance, hundreds or thousands of scans, can be obtained from the population, and then one or more databases can be chosen that best represents that population. Additional publicly available databases of face scans that can be utilized with the present invention include, for example, the Fidentis Database, the FRGCv2 Database, and the ND-2006 Database. In total, the databases contain over 1,000 individuals and, as a result, contain enough facial data to determine the number of masks needed to be designed and/or produced in order to fit every person in the database, as well as the types of general face shapes each mask must have.

Figure 1A:
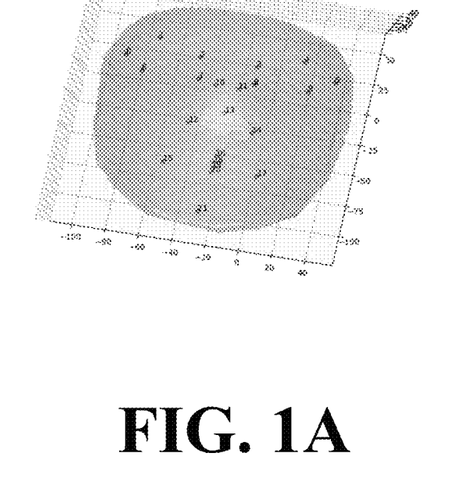
FIGS. 1A-1B illustrate facial landmarks on a 3D facial scan used to produce an anatomically conforming face mask, according to an embodiment of the present invention.
Figure 1B:
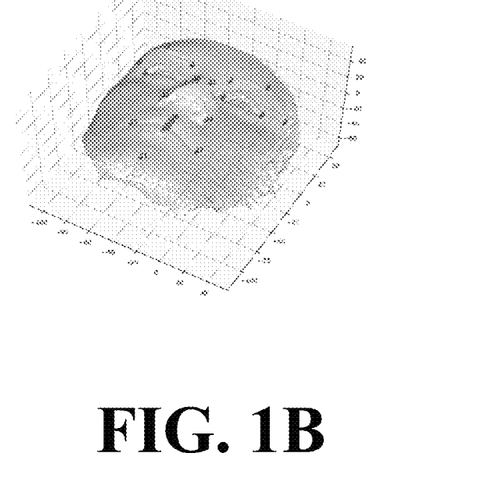

Returning to the non-limiting example of the Bosphorus database, the data therein comes with a set of 22 landmarks associated with fixed positions on each of the 3-D scanned faces. The names of these landmarks are as follows:

0=Outer left eyebrow
1=Middle left eyebrow
2=Inner left eyebrow
3=Inner right eyebrow
4=Middle right eyebrow
5=Outer right eyebrow
6=Outer left eye corner
7=Inner left eye corner
8=Inner right eye corner
9=Outer right eye corner
10=Nose saddle left
11=Nose saddle right
12=Left nose peak
13=Nose tip
14=Right nose peak
15=Left mouth corner
16=Upper lip outer middle
17=Right mouth corner
18=Upper lip inner middle
19=Lower lip inner middle
20=Lower lip outer middle
21=Chin middle Turning now to FIGS. 1A-1B, the locations of the aforementioned landmarks are shown for two different versions (FIG. 1A on the left, FIG. 1B on the right) of the model. It should be appreciated that there are existing methods to determine landmark locations given a 3-D face scan. It should further be appreciated that a clustering method can be utilized based on one or more of these 21 landmarks, rather than comparing full 3-D face scans. However, it should further be appreciated that, at the initial stage, one would not know with certainty the correct facial metric(s) or landmark(s) to use in order to define the various clusters, but these metric(s) or landmark(s) are determined through a computer search and optimization method described herein. A suitable starting point is to use Euclidian distance based on the entire face. Additionally, Wongsup Lee et al., Ergonomic Design and Evaluation of a Pilot Oxygen Mask, Proc. Human Factors and Ergonomics Soc. 57th Annual Meeting 2013, have shown that two of the most important parameters for oral-nasal mask fitting appear to be the length of the face ("Face Length") and the width of the lip ("Lip Width").

Face Length can be approximated, using the available landmarks, by the following equation:

$$FaceLength = \left\| \frac{\text{Inner Left Eyebrow} + \text{Inner Right Eyebrow}}{2} - \text{Chin Middle} \right\|$$

Lip Width can be similarly approximated, using the available landmarks, by the following equation:

$$LipWidth = \|\text{Left Mouth Corner} - \text{Right Mouth Corner}\|$$

Figure 2:
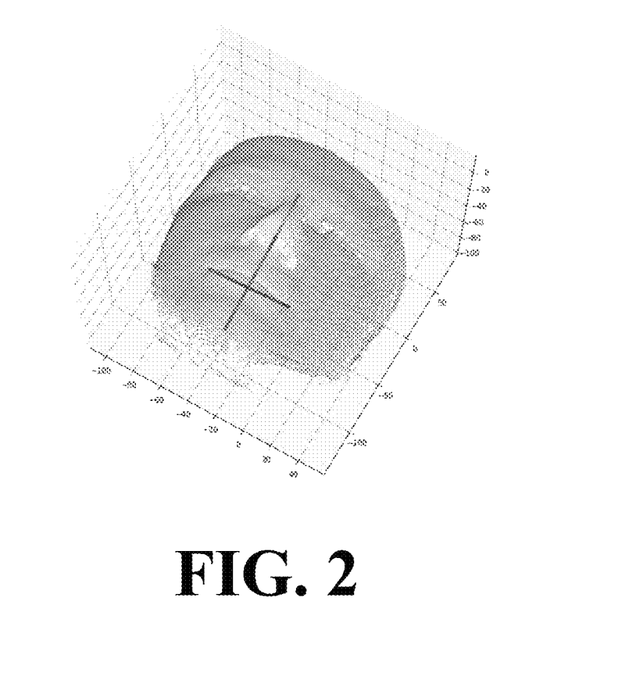
FIG. 2 illustrates the distance measured for face length and the distance measured for lip width, with both distances displayed on a representative face scan.

These quantities are shown for a sample face in FIG. 2. Specifically, line 202 indicates the distance measured for face length, and line 204 indicates the distance measured for lip width.

Figure 3:
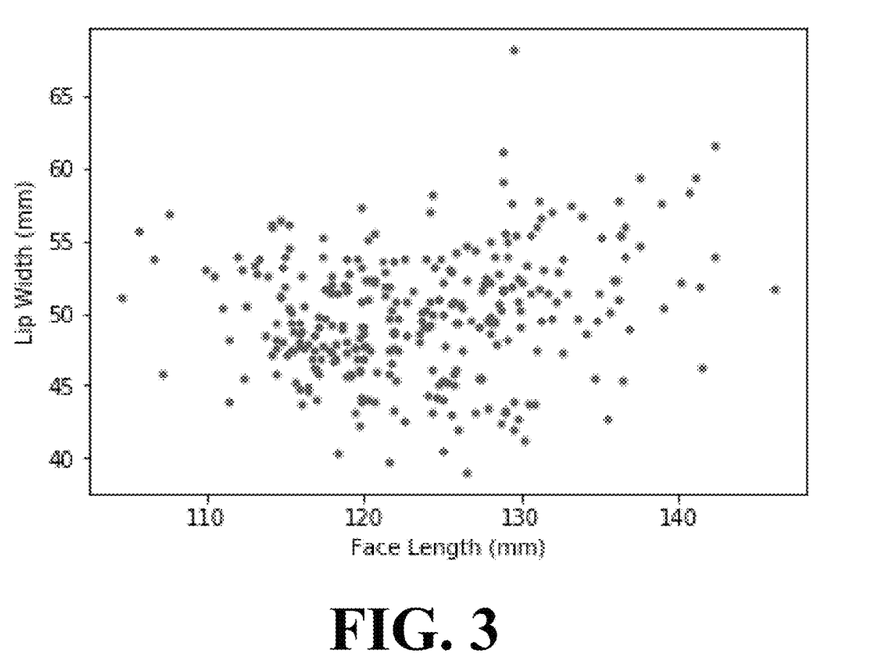
FIG. 3 is a graph that illustrates the relationship between face width measurements (in mm) and lip width measurements (in mm) for each of the faces in the exemplar Bosphorus 3D facial scan data set.

FIG. 3 illustrates the distribution of the 299 faces in the Bosphorus data set based on both Face Length (in mm) and Lip Width (in mm). These faces can then be clustered in a way such that a mask can be provided to any individual that fits with a certain level of accuracy, which may be obtained by measuring the distance between the mask interfacing edge and the face after a virtual alignment of the surfaces. It should be appreciated that the face and the mask can be oriented to have an average surface location and the variations, such as gaps or overlaps, are then summed to get a total (or root mean square) variation of the interface geometry of the face and the mask. It should further be appreciated that face clustering may be done using one or more of the aforementioned 21 landmarks in an identical way to clustering done using full-face 3-D scans. Clustering performed using full-face 3-D scans involves taking each face's full 3-D surface and comparing it to another full face 3-D surface to see which faces are similar to each other. Orientation may be achieved according to, for example, facial landmarks. Similarity may be calculated using, for example, the deviation of the two facial surfaces from each other based on (1) creating a conformal map from one face to the other based on facial landmarks, and (2) measuring the distance between the faces at various locations in between all of the facial landmarks.

Figure 4:
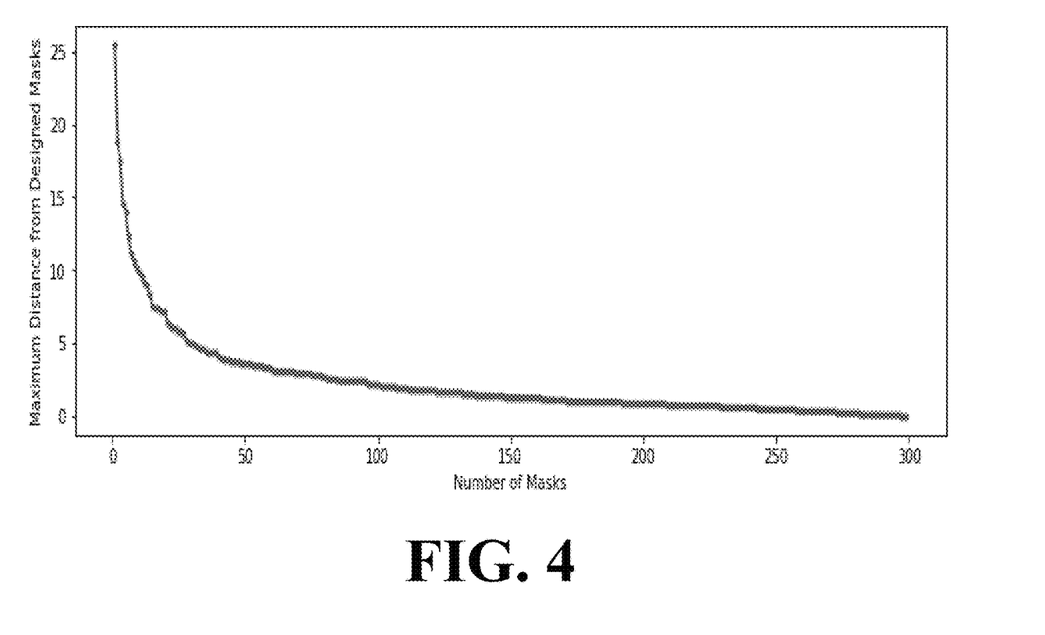
FIG. 4 is a graph that illustrates the relationship between the maximum distance from a face mask designed according to an embodiment of the present invention and the number of such masks, with the maximum distance defined as the sum of the distance mismatch in both the face length and lip width measurements (both measured in mm).

FIG. 4 illustrates the relationship between the maximum distance from a designed mask and the number of masks (and clusters). This maximum distance is the sum of the distance mismatch in Face Length and Lip Width (both measured in mm). In other words, FIG. 4 displays what might be termed the "worst fitting mask," i.e., the designed mask that is the most different from a given individual's face, as a function of the number of masks. One of skill in the art will appreciate that designing and/or producing an increasing number of masks does not linearly correlate with a reduction in magnitude of the "worst fitting mask." Thus, it should be appreciated that there is a suitable range for the Bosphorus data set, such as, for example, in the range of 25-75 masks, that will result in a good fit between any individual in the data set and any one mask in the range of masks. As a result, a finite number of masks can be mass-produced, any one of which will result in an anatomically conformal fit with each individual in the data set.

Figure 5:
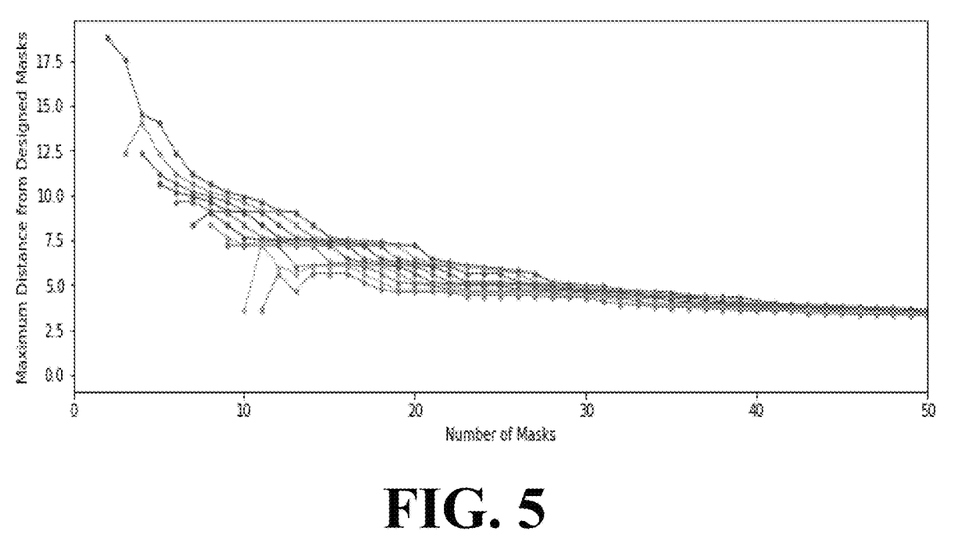
FIG. 5 is a graph that illustrates the relationship between the mismatch associated with the 10 worst fitting masks, as designed according to an embodiment of the present invention, and the number of masks, with a "worst fitting mask" defined as the sum of the distance mismatch in both the face length and lip width measurements (both measured in mm).
Figures 6A, 6B, 6C, 6D:
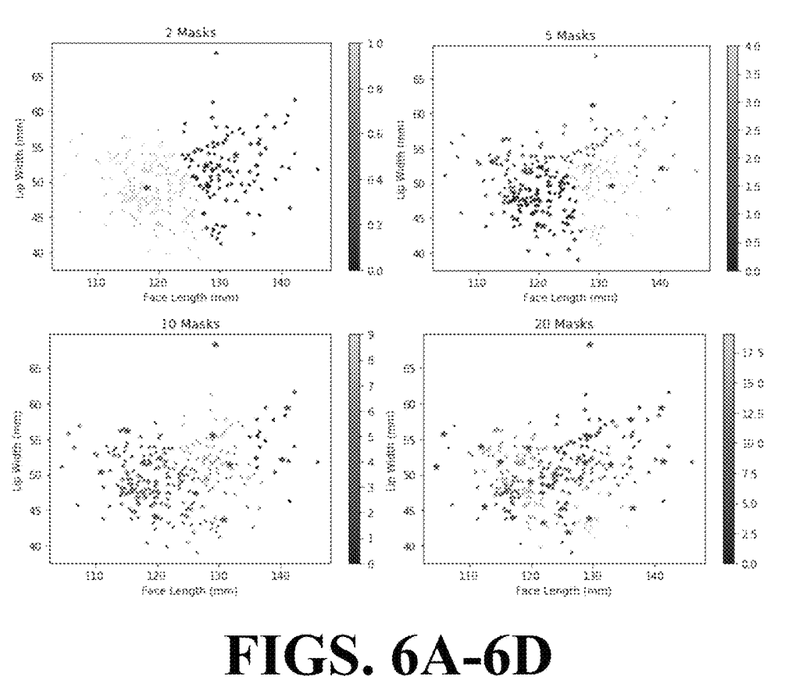
FIGS. 6A-6D illustrate aggregations of the Bosphorus data set example into clusters based on face length measurements and lip width measurements (both measured in mm), with each graph displaying the various clusters that result with a set number of masks (2 masks for FIG. 6A, 5 masks for FIG. 6B, 10 masks for FIG. 6C, and 20 masks for FIG. 6D).

FIG. 5 illustrates a similar relationship as displayed in FIG. 4, namely, the mismatch associated with the 10 "worst fitting masks" as a function of the number of masks. As in FIG. 4, a "worst fitting mask" is defined as the sum of the distance mismatch between the facial surface of the most different face in the cluster to the face at the center of the cluster. FIG. 5 shows that application of a suitable clustering procedure minimizes the mismatch associated with the worst fitting masks and that, as the number of masks increases, the mismatch associated with each of the worst fitting masks approaches zero. In particular, it should be appreciated that, at or around 50 masks, there is minimal difference between each of the 10 worst fitting masks. Thus, a set of 50 masks would result in a good fit between any individual in the Bosphorus data set and any one mask in this set.

FIGS. 6A-6D illustrate aggregations of the Bosphorus data set into clusters based on Face Length and Lip Width. Four different graphs are shown, each displaying the various clusters that result with a set number of masks (2 masks for FIG. 6A, 5 masks for FIG. 6B, 10 masks for FIG. 6C, and 20 masks for FIG. 6D). In each of FIGS. 6A-6D, asterisks represent the data points used to design the various masks. One of skill in the art will appreciate that the clusters change depending on the number of masks in the set.

After suitable clustering has been achieved, using, for example, one or more methods described above, a set of wearable apparatuses can then be designed and produced. The various methods described below are with reference to face masks; however, it should be appreciated that such reference is a non-limiting example and the methods described below, and in the instant specification generally, are applicable to one or more other kinds of wearable apparatuses that require an anatomically conformal fit.

Figure 7:
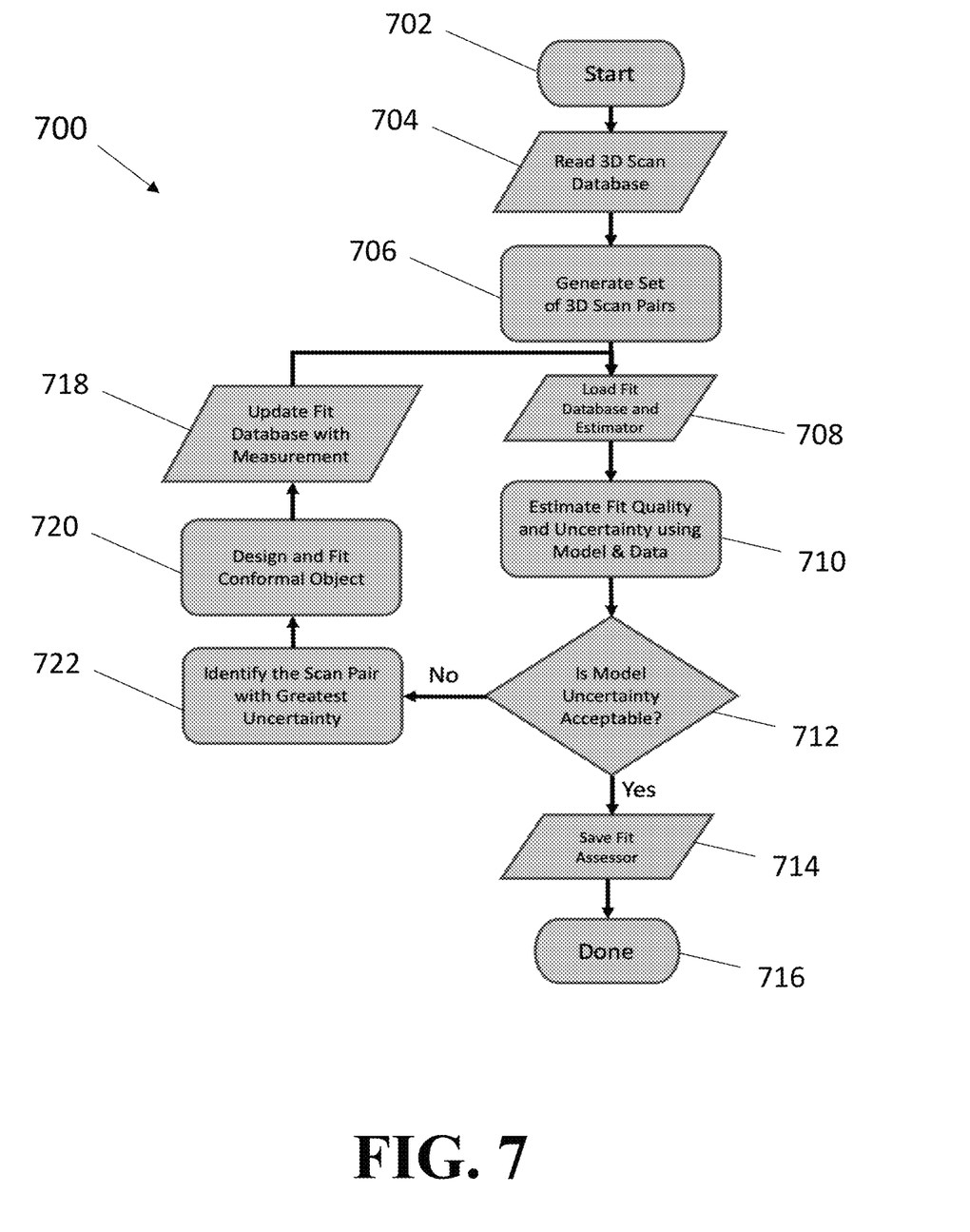
FIG. 7 is a flow diagram illustrating the process for learning a fit assessor, according to an embodiment of the present invention.

Turning now to FIG. 7, a process 700 for training a "fit assessor" is shown. The purpose of the fit assessor is to take two 3-D face scans and return how well, or how poorly, a mask designed for one face will fit on another, different face.

The process starts with a step 702 and first evaluates a database of 3-D face scans at step 704. This database may be one or more of the databases described previously herein, including, as a non-limiting example, the Bosphorus database. The 3-D scans from the database are then arranged into ordered pairs at step 706 such that every 3-D scan appears as the first and second element in the pair with every other scan.

The process further comprises a step 708 of loading the fit database and an estimator from long-term storage. The fit database contains ordered 3-D scan pairs and the associated metrics for fit quality obtained as described previously. The estimator is a software routine that predicts the fit quality metrics from facial landmarks and could include, but is not limited to, Gaussian Processes, Bayesian Neural Networks, or Random Forests.

The process additionally comprises a step 710 of estimating both the fit quality of the face mask and the uncertainty in the fit quality using a model and data. To accomplish this, each pair of masks is examined against the fit database. If the 3-D scan pair is in the database, the fit metrics are obtained from the data. The 3-D scan pairs in the database are used to update the fit estimator using the landmarks associated with the 3-D scans in the pair and the measured fit metrics as labeled training data for the estimator. For all the 3-D scan pairs not in the database, the estimator is used to predict the fit quality and the uncertainty.

This leads to step 712 of deciding whether the uncertainty shown by the model is acceptable. If so, the process continues with step 714 of saving the fit assessor, leading to completion of the process at step 716. However, if the model uncertainty is unacceptable, the process continues with step 718 of identifying the 3-D scan pair that has the greatest uncertainty. Step 720 of designing and fitting a conformal object follows. The process then proceeds to step 722 of updating the fit database with the measurement, resulting in an iterative return to step 708 of loading the now-modified fit database and an estimator.

It should be appreciated that the process 700 obviates the time-consuming and expensive method of designing masks and then directly measuring the sealing pressure of the mask or some other metric to determine how well any given mask fits on any given user. The process 700 further obviates the uncertainty surrounding the alternative method of comparing the 3-D scan of a given user's face with a digital model, such as a computer-aided design (CAD) model, of a mask and estimating the degree of fit based on the amount of intersection between the scan and the digital model. Using a model, as in process 700, reduces or eliminates uncertainty while obviating the requirement of designing and fitting each individual mask.

Figure 8:
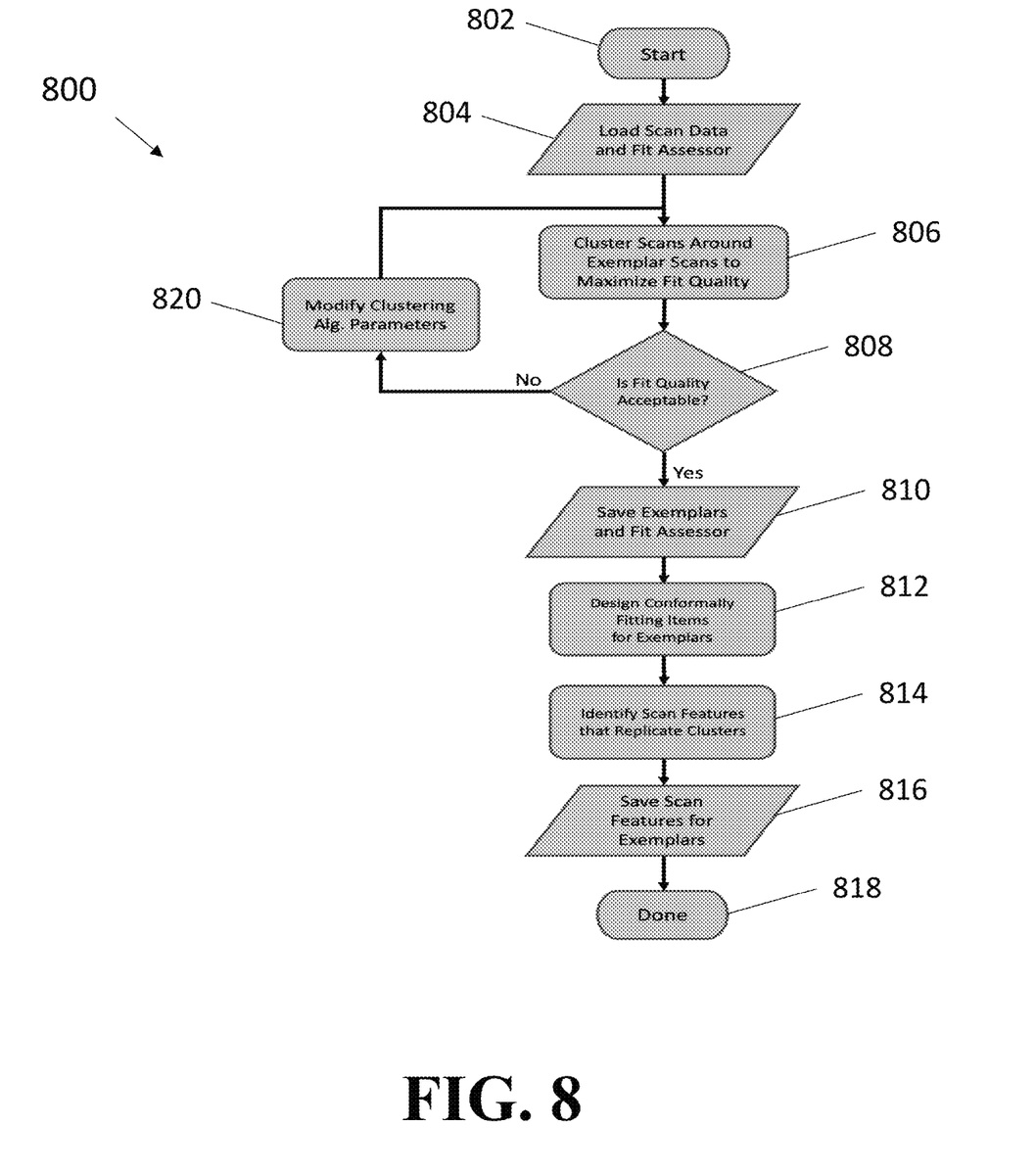
FIG. 8 is a flow diagram illustrating the process for designing an anatomically conforming apparatus, including, for instance, a mask, according to an embodiment of the present invention.

FIG. 8 illustrates a flow chart process 800 for mask design, given a set of scans and a complete fit assessor. The process 800 starts at step 802, and first comprises loading the set of scans and the fit assessor into a computing device at step 804. The process then comprises a step 806 of clustering the set of scans around exemplar scans to maximize fit quality of the putative masks. Using the fit assessor, the quality of fit between every pair of 3-D scans is computed to create a "distance" matrix. This "distance" matrix can be converted to exemplars and clusters using methods known in the art such as, for example, the k-medoids algorithm.

This leads to a step 808 of deciding whether the fit quality generated in step 806 is acceptable. If so, the process continues with a step 810 of saving both the exemplar scans and the fit assessor on the computing device. Step 812 then designs anatomically conforming apparatuses for the exemplar scans. The process further identifies scan features that replicate clusters at step 814, which may be done using methods known in the art, including, for example, PCA, ANOVA, and the like. The process then saves these scan features to be used as future exemplar scans at step 816, leading to completion of the process at step 818. If, however, the fit quality generated in step 806 is not acceptable, the process continues with a step 820 of modifying the clustering algorithm parameters, which leads to an iterative return to step 806 of clustering the set of scans around exemplar scans.

It should be appreciated, therefore, that the process 800 results in an output of a set of scans that can be used to design anatomically conforming wearable apparatuses, such as masks, and also results in identifying a set of features that distinguish clusters from each other.

Figure 9:
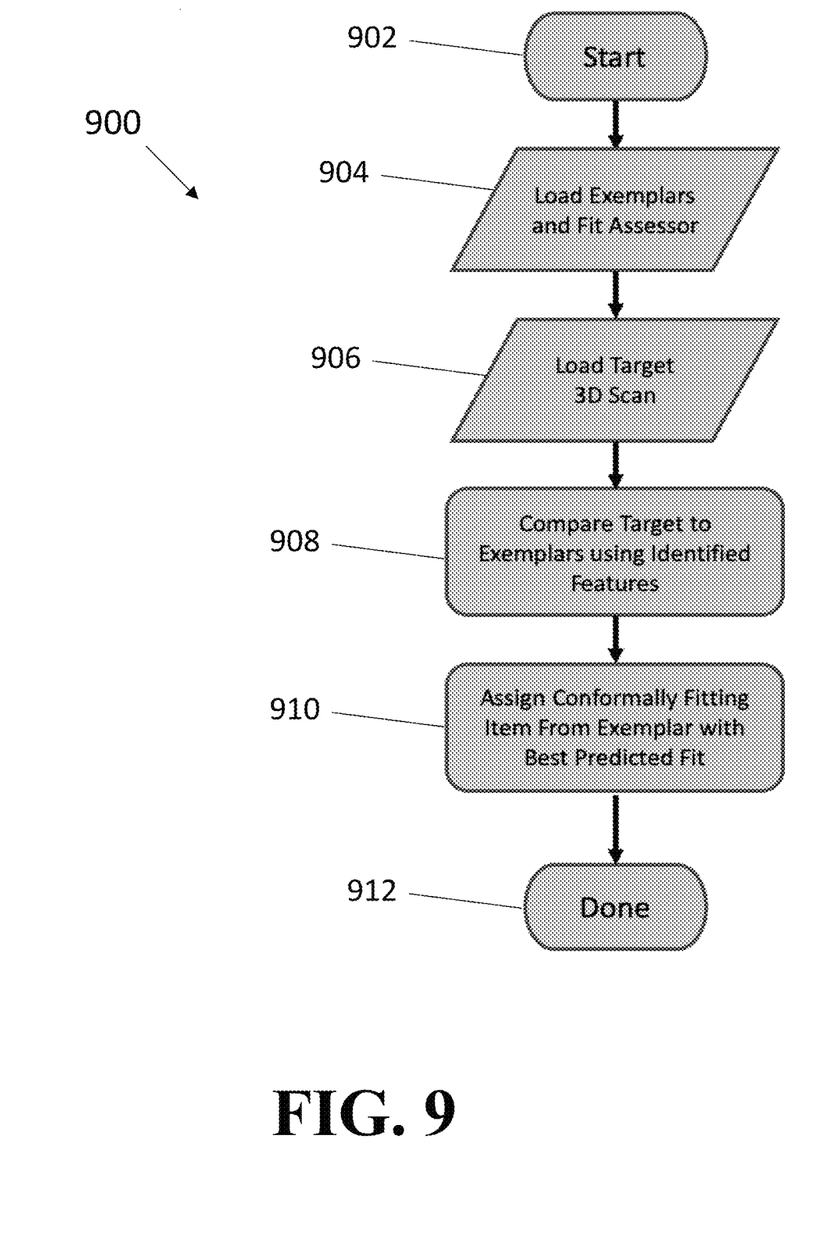
FIG. 9 is a flow diagram illustrating the process for fitting an anatomically conforming apparatus, including, for instance, a mask, in order to identify which specific conforming apparatus in a set that a given user should wear, according to an embodiment of the present invention.

Such scan features are an important part of mask fitting process 900, as shown in FIG. 9. The general purpose of process 900 is to identify a specific mask for a given user to wear based on scan features, exemplar scans, and the fit assessor.

Thus, the process begins at a start step 902 and first comprises loading both the exemplar scans and the fit assessor into a computing device at step 904. The process then comprises a step 906 of loading a target 3-D scan into the computing device. Such scan may be, for example, of a new user's face. The process then continues to a step 908 of comparing the target scan to the exemplar scans using the identified scan features generated in process 800. This comparison is accomplished via the fit assessor described previously. The new 3-D scan is paired with the exemplars identified previously. These pairs are analyzed by the fit assessor to predict the quality of fit. The exemplar with the best quality of fit is selected. Because each exemplar is associated with a conforming apparatus, the conforming apparatus with the best fit can subsequently be assigned at step 910, leading to completion of the process at step 912. It should therefore be appreciated that the process 900 is capable of using scan features to assign a target 3-D scan to a pre-determined cluster. Once this cluster is identified, then a suitable mask corresponding to that cluster can be assigned to the target individual.

It should be appreciated that one or more embodiments of the present invention disclosed herein enable the manufacturing of anatomically conforming cushions that may be coupled or otherwise utilized with existing wearable apparatuses, including, for example, masks. The manufacturing of such cushions may be achieved through a number of methods, including, for instance, 3-D printing/additive manufacturing. Additive manufacturing is favored for production of very low-volume goods, because its cost is much lower for small production runs given the lack of need for a mold, die, or other expensive machine tools. Thus, it lends itself readily to the manufacturing of closely anatomically conforming articles, which due to their highly customized nature may have a very small number of potential customers—in some cases only one, as in some embodiments each customer may receive a customized article unique to them. One of skill in the art will appreciate that the manufacturing of anatomically conforming cushions is an inexpensive and easier alternative than the manufacturing of entire apparatuses, such as masks.

Manufacturing processes such as 3-D printing/additive manufacturing typically entail the production of solid, 3-D objects from a digital file. The creation of the manufactured object is achieved using additive processes rather than subtractive processes. In an additive process, an object is created by laying down successive layers of material until the entire object is created. Each of these layers can be seen in a thinly sliced horizontal cross-section of the eventual object.

Using one or more of these manufacturing methods, an anatomically conforming cushion can be manufactured out of soft, bio-compatible materials. Additive manufacturing techniques have been successfully utilized with various types of materials, including, but not limited to, organic thermoplastics (e.g., polylactic acid or acrylonitrile butadiene styrene), plaster, clay, room-temperature vulcanization materials, paper, metal alloys, and other types of printing material. Medical grade silicone could also be used to manufacture an anatomically conforming cushion. Indeed, due to the expensive nature of medical grade silicone, it is currently expensive and often cost-prohibitive to manufacture wearable apparatuses, such as masks, from such silicone. However, it is relatively inexpensive and cost-feasible to manufacture an anatomically conforming cushion that can be used with standard or off-the-shelf wearable apparatuses.

With reference to the purely non-limiting example of CPAP masks, one of skill in the art will recognize that much of the focus has been on manufacturing suitable masks, rather than manufacturing an anatomically conformal cushion that could be used with standard CPAP masks. Additionally, a skilled artisan will appreciate that custom, anatomically conforming CPAP masks have not been available due to at least two issues. First, scanning a potential user's face has been cost-prohibitive since such scanning required expensive and/or inconvenient scanners. Second, custom CPAP masks are not cost-effective. Even if an accurate scan could be generated of the potential user's face, no cost-effective means of manufacturing the custom mask existed. Current production of CPAP masks utilizes a silicon injection-molding process, resulting in a cost of thousands of dollars per mold.

Various embodiments of the present invention enable resolution of both of the aforementioned issues. Accessible means of scanning a prospective user's face can be achieved with new technology that places an accurate infrared (IR) scanner on mobile phones, tablets, and other electronic devices. This enables broad usage of a low-cost and accurate scanning technology that removes the need for expensive and inconvenient scanners. Additionally, the use of 3-D printing and/or additive manufacturing techniques results in the creation of, for example, a conformal face cushion which can be used with existing, generic (i.e., non-conformal) CPAP masks. In at least one embodiment of the present invention, the face cushion fits on top of the CPAP mask, thereby providing a better and more comfortable fit to the wearer. As discussed above herein, using inexpensive manufacturing processes, coupled with the manufacture of a face cushion as opposed to a full mask, results in a low-cost and easily scalable solution that provides a conformal fit to a wide range of users.

Figure 10:
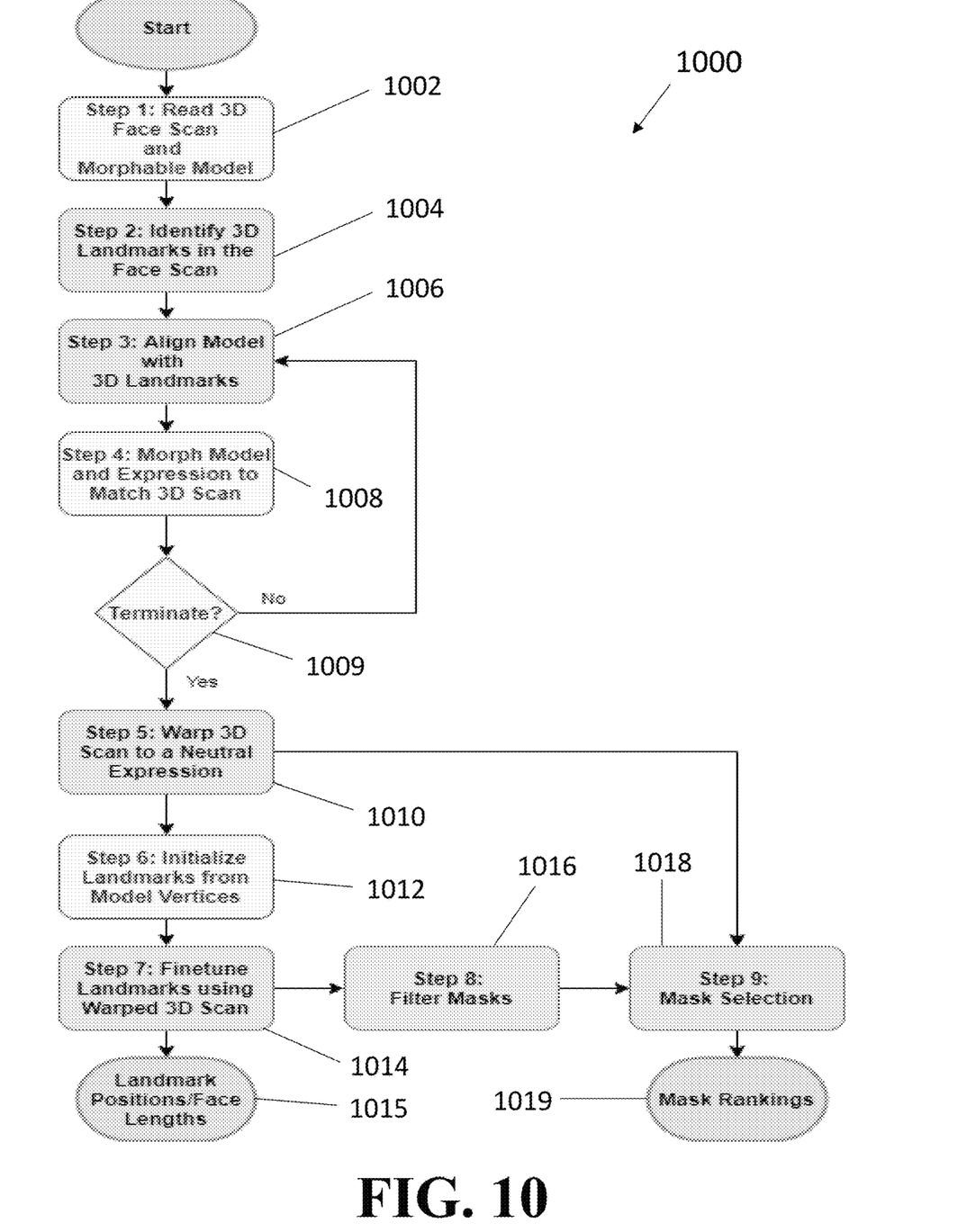
FIG. 10 is a flow diagram illustrating the process for the automated design of an anatomically conforming apparatus, including, for instance, a mask, according to an embodiment of the present invention.

As stated above herein, the design and/or selection of anatomically conforming, mass-producible wearable apparatuses, including, for example, face masks, oral-nasal masks, CPAP masks, and other face-conforming masks, may be automated. Turning now to FIG. 10, a flow diagram is presented illustrating a method 1000 for automatically designing and/or selecting an anatomically conforming apparatus, with special reference to an embodiment in which such an apparatus is a face-conforming mask (e.g., oxygen mask, CPAP mask, etc.).

Generally, the method 1000 reads in a 3D scan of a user's face and returns: (1) the location of pre-determined facial measurements, such as, for instance, length of the nose, and (2) a ranking of mask designs from best- to worst-fitting for that user. The method 1000 may be executed on any suitable system, including, for example, a computing system for running a plurality of computer executable programs to execute the method, where the programs may be contained on a variety of signal-bearing media. Illustrative signal-bearing media include, but are not limited to: (1) information permanently stored on non-writable storage media (e.g., read-only memory devices within a computer such as CD-ROM disks readable by a CD-ROM drive); (2) alterable information stored on writable storage media (e.g., floppy disks within a diskette drive or hard-disk drive, solid state storage devices); and (3) information stored on non-transitory computer readable medium and conveyed to a computer by a communications medium, such as through a computer or telephone network, including wireless communications.

At step 1002, a 3D face scan of a user is taken and assembles a morphable face model, both of which can be stored in, for example, computer or system memory. A typical morphable model includes: (1) a mean face which is a 3D model of the average face obtained from a data set (such as, for instance, any of the data sets described above herein); (2) a set of shape modes that capture the deformations of the face observed in the data; and (3) a set of expression modes that captures the deformations in a face due to different emotions.

It will be appreciated that any given morphable model may contain other components if necessary to design a face mask for a particular purpose. It will further be appreciated that morphable models, their creation from data, and the different features such models contain will be familiar to those of skill in the art. See, e.g., A. Patel and W. Smith, "3D morphable face models revisited," 2009 IEEE Conference on Computer Vision and Pattern Recognition (2009). Loading 3D face scans is also well-known to a skilled artisan, provided, however, that the scan is in a common format, such as, e.g., a Stereolithography (STL) or Polygon (PLY) format, for which open-source readers are readily available.

At the outset of the method 1000, a morphable model trained on a standard population is used. However, as 3D scans are processed, the model is refined to best fit the user or users for which the mask is being designed.

At step 1004, 3D landmarks in the user's 3D face scan is automatically identified so that a rough alignment of the 3D scan and the morphable model can be performed in step 1006. The step 1004 further includes identifying the position (x,y) (i.e., row and column) of the pixel associated with each 3D facial landmark.

It is well-known in the art to perform the aforementioned step in 2D by running a facial landmark detector (e.g., https://github.com/davisking/dlib-models) on a 2D image of the subject (e.g., https://pypi.org/project/eos-py/). However, unlike those 2D-based approaches, the method 1000 returns the 3D location of landmarks by, in a non-limiting example, (1) rendering, for a given 3D face scan, the model as a 2D image and additionally recording camera parameters (i.e., the transformation from 3D space to 2D image pixels); (2) supplying the 2D image to a 2D facial landmark detector to record pixel locations of the facial landmarks; (3) given the camera parameters and the 2D locations of the landmarks, projecting those landmarks on to the 3D face scan by finding the ray that intersects the camera, the 2D pixel location of each landmark, and the closest point on the 3D face for each landmark; and (4) saving that closest point. If a location on the 3D face scan is not found (i.e., the ray through a given 2D pixel location does not intersect the 3D face scan), the entire ray is saved.

Step 1006 then then applies a scaled orthographic transform to the morphable model to best match the landmarks on that model with the identified and saved points and/or rays from step 1004. It should be appreciated that the current state of the art is to identify the location of facial landmarks on a morphable model by hand. To perform the matching and alignment, the distance between the landmark locations on the morphable model and the landmark locations on the 3D scan (or the ray that intersects the 2D location of the landmark) is minimized. Although fitting a scaled orthographic transform to 2D data is known to a skilled artisan (see, for example, the eos-py code repository), step 1006 performs the alignment in 3D and can also perform the alignment with rays as well as points.

A specific, non-limiting example of the aforementioned fitting/alignment procedure follows, with four sub-steps. First, given the current location of the landmarks on the 3D model, the closest point on the corresponding landmark ray is found. Second, an affine transform is found that, when applied to the 3D model, minimizes the distance between the landmarks on the 3D model and the landmarks on the face scan or the closest point on the ray. It should be appreciated that finding an affine transform in such a context involves solving a least squares problem, which is well-known to a skilled artisan. Third, a scaled orthographic transform is found that is closest to the affine transform previously identified. To accomplish this, let the affine transform have the form x'=Ax+b, where x is the original location of a point and x' is the location after the transform is applied. Decompose A using the singular value decomposition (SVD) so $A=U\Sigma V^T$. Let $$s = \frac{1}{3}\sum_{k=1}^{3}\sum_{ki}.$$

Then, the scaled orthographic transform has the form: $x'=sUV^Tx+b$. Fourth, if the change in the orthographic transform between iterations is below a pre-determined threshold, then the procedure is stopped. Otherwise, the procedure is repeated from the first sub-step.

Next, in step 1008, the morphable model face is deformed to best fit the 3D face scan. This can be achieved through one or more algorithms known to a skilled artisan. A non-limiting example of a process for deforming the morphable model face is as follows: First, for each vertex in the morphable face model, the closest corresponding point on the 3D face scan is found. Second, let the location of each vertex in the morphable model be defined as follows: $v_i = \overline{v}_i + \sum_{k=1}^{N} a_k u_{ik} + \sum_{j=1}^{N} b_j w_{ij}$ where $\overline{v}_i$ is the location of the i-th vertex in the mean face, $u_{ik}$ is the deformation of the i-th vertex by the k-th shape mode, and $w_{ij}$ is the deformation applied by the j-th expression mode. The coefficients $a_k$ and $b_j$ are the coefficient associated with each mode. Finding the coefficients that minimize the distance requires solving a least squares problem, a problem that is well-known in the art. Third, the first sub-step is repeated until either convergence (i.e., the change in coefficients falls below a threshold) or a pre-determined number of iterations occurs.

The output of step 1008 is a "warped" 3D face model with a new set of coefficients. At decision point 1009, if the converged coefficients are within a pre-determined threshold, then the method 1000 proceeds to step 1010. Otherwise, the method reverts to step 1006 using the warped face model identified in step 1008.

Next, step 1010 maps the user's face back to a neutral expression to remove the impact that the expression can have on measured landmark distances. To do so, the location of each point on the 3D face scan must be expressed in the coordinates of the 3D model. In at least one embodiment, this can be accomplished by expressing the position of each vertex in the 3D face scan in the coordinate system defined by the 3D scan. The following procedure is a non-limiting example of how this can be done: First, for each vertex on the 3D scan, the nearest vertex on the morphable face model is computed. If this distance is larger than a user-determined threshold (e.g., greater than 2 cm), then the vertex is removed from the 3D scan. It should be appreciated that these points do not correspond to relevant points on the face, such as, for instance, the back of the head, hair, or clothing. Second, for each triangle (i.e., the two-dimensional object formed by three connected vertices in the mesh) in the 3D face model, the normal direction is computed. Then, the distance is found between any point on the triangle to each vertex on the 3D scan along the normal direction. The intersection point with the triangle is stored using a Barycentric coordinate system, which is a coordinate system well-known in the art that describes the location of a point on a triangle with respect to the three vertices in the triangle. The distance from the triangle along the normal direction is also saved. Vertices that are not contained within the face are considered to have infinite distance. Third, each vertex in the 3D face scan is associated with the triangle to which it is closest. Each point in the 3D scan is then expressed in terms of the Barycentric coordinates of the corresponding triangle and the deviation in the normal direction, as opposed to the original Euclidean (x, y, z) coordinates. Fourth, the 3D morphable model is warped to be a neutral expression by setting $b_j=0$ for all j. Fifth, the Euclidean coordinates of each vertex in the 3D face scan are then reconstructed from the saved Barycentric coordinates and deviation in the normal direction. As a result of the warped 3D model, the location of the triangle vertices and the normal direction will change, so the resulting Euclidean coordinates will differ. The final result of the above-mentioned procedure is a warped version of the original 3D face scan with the expression removed/made neutral.

Then, step 1012 identifies the initial location of the landmarks used for face measurements and mask fitting based on the position of the 3D morphable model. Identifying landmark points on a morphable model is a common task in the art and can be achieved by, e.g., manually selecting vertices (or a point between vertices) on the morphable model. Given the vertex number of each landmark on the morphable model, the location of that vertex is found after the previous steps in the method 1000 have been performed to extract the landmark location.

Next, step 1014 uses the facial landmarks as initial points to extract face measurements. Although it is known in the art to use landmarks to compute measurements, errors in model warping processes will be carried over to these measurements. To prevent such error propagation, step 1014 performs an analysis on the warped 3D scan to correct some, or all, of any errors introduced in previous steps. In at least one embodiment, this step includes, but is not limited to, the following refinement sub-steps: First, to compute the width of the nose, each point on the warped 3D scan associated with a "nose vertex" (i.e., a vertex in the 3D model pre-determined to contain the nose) is associated with a corresponding point on the other side of the nose by reflecting over the center of the face. The center of the face is determined by fitting a plane to the line of vertices in the center of the model. The width of the nose is determined by the maximum distance between any two points in this set. Second, to compute the length of the nose, the base of the nose is first found. Rather than using the location in the 3D model, the strip of points that are closest to the centerline in the 3D model is extracted. A quadratic model is fit to this strip of points and the minimum point is chosen as the nose base. The rationale behind this approach is to find the junction between the upper lip and the bottom of the nose. From this point, the length of the nose is measured by finding the vertical distance to the highest point on the nose. Third, to compute the length of the face (e.g., from the chin area to the nose bridge), a strip along the centerline of the face is extracted in both the chin region and the nose bridge region. A quadratic model is fit to this strip of points and the minimum value is used.

One of skill in the art will appreciate that additional sub-steps can be defined and used for other facial measurements and/or landmarks. It should further be appreciated that the method described herein does not rely upon pre-determined locations on the face model to measure distances. Rather, these locations are used as initial guesses that are later refined on a full 3D model. The updated landmarks and facial measurements are then carried over to step 1016 below, and may also be output to the user at step 1015.

The inputs to step 1016 are a set of masks and the criteria used to filter poorly fitting masks based on the measured face lengths. Initially, the filter criteria are determined by subject matter experts (SMEs). As the method 1000 processes more data, it generates a database that contains the face measurements as well as the mask that was eventually chosen. At this point, the SME-based rules are adjusted or replaced by mask filtering rules learned from data as will be described below. Even small amounts of data (e.g., as small as one data point) can be used to adjust the parameters defined in the SME-provided rules (e.g., a large mask may initially have a face length of 100 mm but may be adjusted up to 105 mm based on data). New rules can be established using algorithms like the CN2 induction algorithm (see, e.g., P. Clark and T. Niblett, "The CN2 induction algorithm," *Machine Learning* 3.4: 261-83 (1989)), or more modern variants, and compared against the SME-defined rules to judge their efficacy.

Finally, step 1018 implements a mask selection process. In this step, a 3D scan of any feasible masks from step 1016 are loaded into memory. These models are subdivided into the vertices that should be in contact with the face and the remainder of the model. The iterative closest point (ICP) algorithm, which is known in the art, then used to bring the chosen mask into the best possible alignment with the face. To both limit the size of the problem and avoid non-sensical results (e.g., an oxygen mask being placed on the top of the head simply because that region matched the mask contours well), the face model is used to remove any points in the 3D scan that do not correspond with regions where a mask should rest. It should be appreciated that deciding where a mask should rest can be done by marking the locations on the morphable model the regions where a mask should be on an individual's face. Rankings of the feasible masks are then output to the user at step 1019.

It should be appreciated that the ICP algorithm has an objective function, which is different than what is commonly known and/or utilized in the art. That is, uniform weighting of all points equally is common in using the ICP algorithm. However, in the method described above, and in particular step 1018, each part of the face is weighted differently. These weights are initially chosen by an SME, but later refined such that the residual produced by the ICP algorithm is the smallest, or is as small as possible, for the mask that is actually selected. It should therefore be appreciated that such a weighing process can identify subtle but important issues that are relevant for mask fit, such as, for instance, air leaking out into the eyes. These issues can then be fixed by, e.g., weighting the fit more heavily in the region between the nose and the eyes than elsewhere on the face.

Embodiments of the present invention have been described with particular reference to face masks, including, for example, oral-nasal masks, but it should be appreciated that the invention in its embodiments is applicable to other anatomically conforming wearable apparatuses that may be worn, for instance, on areas of the body other than the face. Such apparatuses may include, for example, shoes, gloves, earplugs, chair seats, and the like.

These and other objectives and features of the invention are apparent in the disclosure, which includes the above and ongoing written specification.

Any of the processes, methods, and algorithms described in any of the preceding sections may be embodied in, and fully or partially automated by, code instructions executed by one or more computer systems or computer processors comprising computer hardware. The processes and algorithms may be implemented partially or wholly in application-specific circuitry.

Further, any process descriptions, elements, or units in the diagrams described herein and/or depicted in the attached figures should be understood as potentially representing units, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated.

The invention is not limited to the particular embodiments illustrated in the drawings and described above in detail. Those skilled in the art will recognize that other arrangements could be devised. The invention encompasses every possible combination of the various features of each embodiment disclosed. One or more of the elements described herein with respect to various embodiments can be implemented in a more separated or integrated manner than explicitly described, or even removed or rendered as inoperable in certain cases, as is useful in accordance with a particular application. While the invention has been described with reference to specific illustrative embodiments, modifications and variations of the invention may be constructed without departing from the spirit and scope of the invention as set forth in the following claims.

We claim:

1. A method for the automated design of a set of anatomically conformal apparatuses, the method comprising:
    obtaining a set of three-dimensional (3-D) anatomical scans that represent a predetermined population of individuals;
    applying an iterative clustering algorithm to the set of 3-D anatomical scans, thereby producing one or more clusters of scans based on a plurality of facial measurements from the set of 3-D anatomical scans;
    evaluating the one or more clusters of scans using one or more metrics to find an anatomically conforming apparatus that fits a group of users, wherein the one or more metrics comprise a minimum level of fit and/or a maximum level of applied pressure to achieve a fit; and
    designing the anatomically conformal apparatus for each of the one or more clusters of scans, thereby creating a set of anatomically conformal apparatuses.

2. The method of claim 1, wherein the anatomically conformal apparatus is an oral-nasal mask.

3. The method of claim 1, wherein the set of anatomically conformal apparatuses is capable of being mass-produced.

4. The method of claim 1, wherein at least one of the sets of anatomically conformal apparatuses fit every individual in a large population.

5. The method of claim 1, further comprising:
    evaluating the iterative clustering algorithm to determine one or more ways to group the set of 3-D anatomical scans into the one or more clusters of scans.

6. The method of claim 5, wherein the evaluating step comprises utilization of a computer model.

7. A method for the automated design of a set of anatomically conformal apparatuses, the method comprising:

obtaining a set of three-dimensional (3-D) anatomical scans that represent a predetermined population of individuals;

applying an iterative clustering algorithm to the set of 3-D anatomical scans, thereby producing one or more clusters of scans; and designing an anatomically conformal apparatus for each of the one or more clusters of scans, thereby creating a set of anatomically conformal apparatuses, wherein the one or more clusters of scans are grouped according to one or more physical parameters.

8. The method of claim 7, wherein the one or more physical parameters are set to an initial group of parameters comprising mouth width and a distance from the nose bridge to a predetermined spot below the lower lip.

9. The method of claim 8, further comprising:
creating one or more groupings of the set of 3-D anatomical scans by determining, using the initial group of parameters, which scans in the set of 3-D anatomical scans are most similar.

10. The method of claim 7, wherein the one or more physical parameters are in any number of dimensions.

11. The method of claim 1, further comprising comparing similarity of at least a first scan in the set of 3-D anatomical scans with at least a second scan in the set of 3-D anatomical scans, the similarity calculated using a deviation of anatomical surfaces from the first scan to the second scan.

12. The method of claim 11, wherein the deviation is calculated by creating a conformal map from the first scan to the second scan that is based on anatomical landmarks, and by measuring the distances at predefined locations in between the anatomical landmarks.

13. The method of claim 1, further comprising:
identifying a central scan within each of the one or more clusters of scans, thereby generating a set of central scans.

14. The method of claim 13, wherein the designing step further comprises:
utilizing the set of central scans.

15. The method of claim 1, wherein all of the scans in each of the one or more clusters are anatomically similar.

16. A method for producing a set of anatomically conforming apparatus, the method comprising:
clustering three-dimensional (3-D) facial scans for a group of users based on a plurality of facial measurements from the 3-D facial scans;
evaluating the clustering using one or more metrics to find a set of anatomically conforming apparatuses that fit the group of users, wherein the one or more metrics comprise a minimum level of fit and/or a maximum level of applied pressure to achieve a fit; and
producing the set of anatomically conforming apparatuses.

17. The method of claim 16, wherein the clustering further comprises matching the 3-D facial scans against a plurality of faces from a population database.

18. The method of claim 16, wherein the plurality of facial measurements comprises mouth width measurements and/or distance measurements from the nose bridge to a predetermined spot below the lower lip.

19. The method of claim 16, wherein the evaluating further comprises utilizing either a physical measurement of fit or a fit evaluation model to determine the set of anatomically conforming apparatuses that fit the group of users.

20. The method of claim 16, wherein the minimum level of fit is met if no point on any user's face in the group of users experiences an amount of force greater than 2 psi.

21. A method for the automated design of an anatomically confirming apparatus, the method comprising:
assembling a morphable face model based on at least one three-dimensional (3-D) face scan of a user;
identifying a plurality of 3-D landmarks, and a pixel position associated with each of the plurality of 3-D landmarks, in the at least one 3-D face scan;
applying a scaled orthographic transform to the morphable face model to match facial landmarks on the morphable face model to the plurality of 3-D landmarks;
fit the morphable face model to the at least one 3-D face scan;
warp the at least one 3-D face scan to make the user's expression neutral;
determining locations of the facial landmarks on the morphable model;
refining, by the at least one warped 3-D face scan, the locations of the facial landmarks on the morphable model;
selecting, by an iterative closest point (ICP) algorithm, an anatomically confirming apparatus that best fits the refined locations of the facial landmarks.

22. The method of claim 21, wherein the identifying further comprises:
rendering, for the at least one 3-D face scan, the morphable face model as a two-dimensional (2-D) image;
recording camera parameters;
supplying the 2-D image to a 2-D facial landmark detector to record 2-D landmark locations;
projecting the 2-D landmark locations on to the at least one 3-D face scan;
determining, by the camera parameters and the 2-D landmark locations, the pixel position associated with each of the plurality of 3-D landmarks.

* * * * *